(12) United States Patent
Kiani

(10) Patent No.: US 11,058,942 B2
(45) Date of Patent: Jul. 13, 2021

(54) AVATAR-INCENTIVE HEALTHCARE THERAPY

(71) Applicant: MASIMO CORPORATION, Irvine, CA (US)

(72) Inventor: Massi Joe E. Kiani, Laguna Niguel, CA (US)

(73) Assignee: Masimo Corporation, Irvine (GA)

( * ) Notice: Subject to any disclaimer, the term of this patent is extended or adjusted under 35 U.S.C. 154(b) by 0 days.

(21) Appl. No.: 17/118,323

(22) Filed: Dec. 10, 2020

(65) Prior Publication Data

US 2021/0086068 A1  Mar. 25, 2021

Related U.S. Application Data

(63) Continuation of application No. 16/402,903, filed on May 3, 2019, now Pat. No. 10,881,951, which is a continuation of application No. 14/571,286, filed on Dec. 15, 2014, now Pat. No. 10,279,247.

(60) Provisional application No. 61/916,136, filed on Dec. 13, 2013.

(51) Int. Cl.

| A63F 13/212 | (2014.01) |
| A61B 5/00 | (2006.01) |
| A61B 5/0205 | (2006.01) |
| A61B 5/1455 | (2006.01) |
| A61B 5/021 | (2006.01) |
| A61B 5/145 | (2006.01) |
| A61B 5/024 | (2006.01) |

(52) U.S. Cl.
CPC .......... *A63F 13/212* (2014.09); *A61B 5/0205* (2013.01); *A61B 5/744* (2013.01); *A61B 5/0022* (2013.01); *A61B 5/021* (2013.01); *A61B 5/024* (2013.01); *A61B 5/1455* (2013.01); *A61B 5/14532* (2013.01)

(58) Field of Classification Search
CPC ...................................................... A63F 13/212
USPC ........................................................... 434/257
See application file for complete search history.

(56) References Cited

U.S. PATENT DOCUMENTS

| 9,022,930 | B2 * | 5/2015 | Sachanandani | ...... A61N 1/3702 600/301 |
| 2012/0189990 | A1 * | 7/2012 | Bavelier | .................. G09B 5/06 434/188 |
| 2014/0004492 | A1 * | 1/2014 | O'Reilly | ................ G16H 20/30 434/236 |
| 2014/0275835 | A1 * | 9/2014 | Lamego | ................ G16H 50/30 600/301 |
| 2014/0323899 | A1 * | 10/2014 | Silberstein | ............. A61B 5/165 600/544 |

FOREIGN PATENT DOCUMENTS

KR   2004083759 A  * 10/2004

* cited by examiner

*Primary Examiner* — Kesha Frisby
(74) *Attorney, Agent, or Firm* — Knobbe Martens Olson & Bear, LLP

(57) ABSTRACT

An avatar-incentive healthcare therapy system has a physiological monitor for generating a physiological parameter indicative of physical health. An academic test for generating a test score is indicative of mental acuity. The avatar has outward characteristics and game play capabilities proportional to the physiological health and the mental acuity so as to incentivize improved physical health and academic performance.

19 Claims, 5 Drawing Sheets

AVATAR-INCENTIVE HEALTHCARE THERAPY

INCORPORATION BY REFERENCE TO ANY PRIORITY APPLICATIONS

The present application claims priority benefit under 35 U.S.C. § 119(e) to U.S. Provisional Patent Application Ser. No. 61/916,136 filed Dec. 13, 2013, titled Avatar Incentive Video Game, hereby incorporated in its entirety by reference herein.

BACKGROUND OF THE INVENTION

Medical device manufacturers are continually increasing the processing capabilities of patient monitors, specifically of patient monitors that process signals based on attenuation of light by patient tissue. In general, such patient monitoring systems include one or more optical sensors that irradiate tissue of a patient and one or more photodetectors that detect the radiation after attenuation thereof by the tissue. The sensor communicates the detected signal to a patient monitor, where the monitor often removes noise and preprocesses the signal. Advanced signal processors then perform time domain and/or frequency domain processing to determine measurements of blood constituents and other physiological parameters of the patient.

Manufacturers have advanced basic pulse oximeters that determine measurements for blood oxygen saturation ("SpO2"), pulse rate ("PR") and pethysmographic information, to read-through-motion oximeters, to co-oximeters that determine measurements of many constituents of circulating blood. For example, Masimo Corporation of Irvine Calif. ("Masimo") manufactures pulse oximetry systems including Masimo SET® low noise optical sensors and read through motion pulse oximetry monitors for measuring SpO2, PR, perfusion index ("PI") and others. Masimo sensors include any of LNOP®, LNCS®, SofTouch™ and Blue™ adhesive or reusable sensors. Masimo oximetry monitors include any of Rad-8®, Rad-5®, Rad®-5v or SatShare® monitors.

Many innovations improving the measurement of blood constituents are described in at least U.S. Pat. Nos. 6,770,028; 6,658,276; 6,157,850; 6,002,952; 5,769,785 and 5,758,644, which are assigned to Masimo and are incorporated by reference herein. Corresponding low noise optical sensors are disclosed in at least U.S. Pat. Nos. 6,985,764; 6,088,607; 5,782,757 and 5,638,818, assigned to Masimo and hereby incorporated in their entirety by reference herein.

Masimo also manufactures more advanced co-oximeters including Masimo Rainbow® SET, which provides measurements in addition to SpO2, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Masimo's advanced blood parameter monitors include Masimo Radical-7™, Rad-87™, and Rad-57™ monitors as well as Pronto and Pronto-7 spot check monitors.

Innovations relating to these more advanced blood parameter measurement systems are described in at least U.S. Pat. Nos. 7,647,083; 7,729,733; U.S. Pat. Pub. Nos. 2006/0211925; and 2006/0238358, assigned to Cercacor Laboratories of Irvine, Calif. ("Cercacor") and hereby incorporated in their entirety by reference herein.

Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated in their entirety by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated in their entirety by reference herein. Advanced pulse oximetry systems including Masimo SET® low noise optical sensors and read through motion pulse oximetry monitors for measuring SpO2, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Cercacor Laboratories, Inc., Irvine, Calif. (Cercacor) and all incorporated in their entirety by reference herein. An advanced parameter measurement system that includes acoustic monitoring is described in U.S. Pat. Pub. No. 2010/027 4099, filed Dec. 21, 2009, titled Acoustic Sensor Assembly, assigned to Masimo and incorporated in its entirety by reference herein.

Advanced blood parameter measurement systems include Masimo Rainbow® SET, which provides measurements in addition to SpO2, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Advanced parameter measurement systems may also include acoustic monitoring such as acoustic respiration rate (RRa™) using a Rainbow Acoustic Sensor™ and Rad-87™ monitor, available from Masimo. Such advanced pulse oximeters, low noise sensors and advanced parameter systems have gained rapid acceptance in a wide variety of medical applications, including surgical wards, intensive care and neonatal units, general wards, home care, physical training, and virtually all types of monitoring scenarios.

SUMMARY OF THE INVENTION

An avatar-incentive healthcare therapy system has a physiological monitor for generating a physiological parameter indicative of physical health. An academic test for generating a test score is indicative of mental acuity. The avatar has outward characteristics and game play capabilities proportional to the physiological health and the mental acuity so as to incentivize improved physical health and academic performance.

DETAILED DESCRIPTION OF THE PREFERRED EMBODIMENT

Figure 1B:
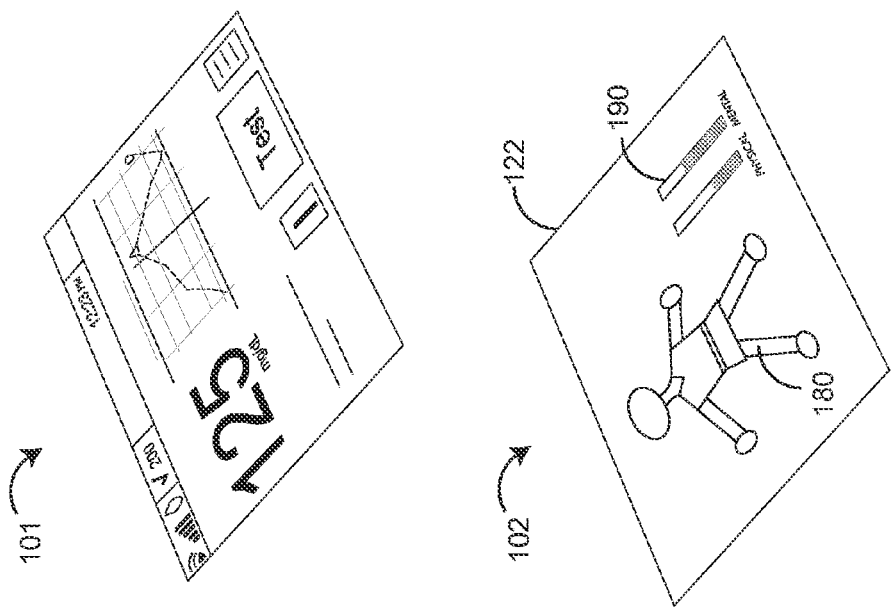
FIGS. 1A-B are perspective views of a physiological monitor and corresponding monitor screens incorporating avatar-incentives for healthcare therapy.
Figure 1A:
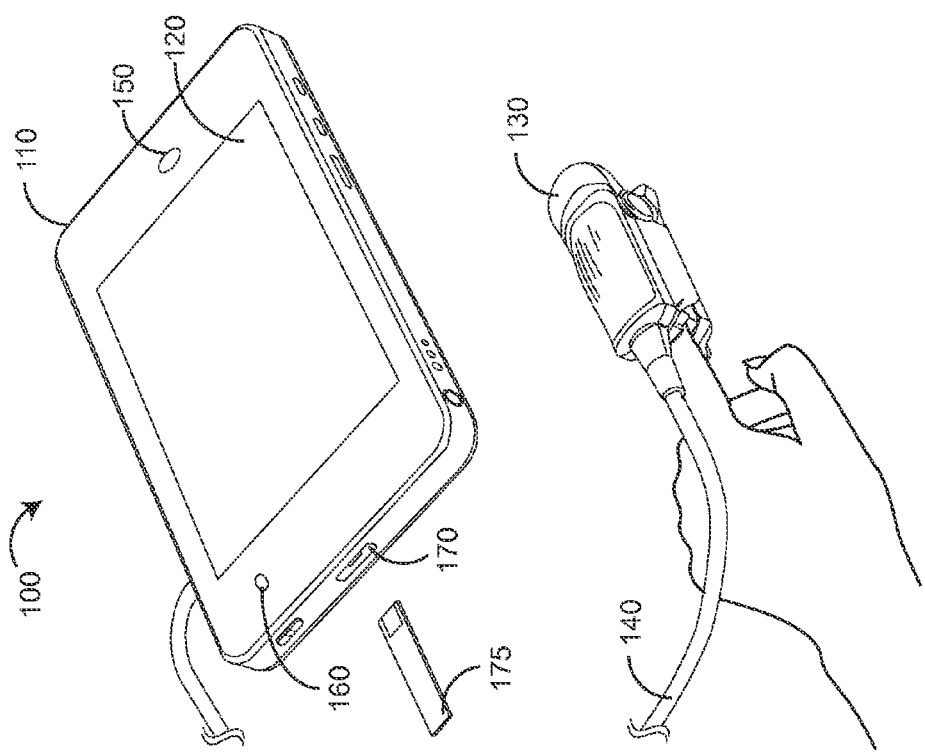

FIGS. 1A-B illustrate a physiological monitor 100 and corresponding monitor screens 101, 102 incorporating avatar-incentives for encouraging physical and mental fitness. As shown in FIG. 1A, the physiological monitor 100 has a hand held processing device 110, a touch screen display 120, a noninvasive optical sensor 130, a sensor cable 140 electrically and mechanically interconnecting the processing device 110 and the sensor 130, a monitor-integrated test strip reader 170 that accepts test strips 175, one or more input keys 150 and an integrated camera 160 among other features. An optical sensor is described in detail with respect to U.S. patent Ser. No. 13/646,659 titled Noninvasive Blood Analysis System, filed Oct. 5, 2012, assigned to Cercacor and incorporated in its entirety by reference herein. A blood glucose monitor is described in detail with respect to U.S. patent Ser. No. 13/308,461 titled Handheld Processing Device Including Medical Applications for Minimally and Noninvasive Glucose Measurements, filed Nov. 30, 2011, assigned to Cercacor and incorporated in its entirety by reference herein. A blood glucose monitor and sensor are described in U.S. Ser. No. 13/473,477 titled Personal Health Device, filed May 16, 2012, assigned to Cercacor and incorporated in its entirety by reference herein.

As shown in FIG. 1B, in an embodiment, the touch screen display 120 has a physiological monitor display mode 101 and an incentive game play mode 102. In a physiological monitor display mode 101, the monitor displays measured physiological parameters. In an incentive game play mode 102, the monitor constructs a video player avatar 180 having physical and mental strengths 190 based upon incentivizing criteria described below. In an embodiment, the avatar is inserted into physiological monitor-based video games according to its strengths 190 or exported externally to video games running on standalone video game systems or from the cloud, as described with respect to FIGS. 3-5, below.

Also shown in FIG. 1B, in an incentive game play mode 102, the touch screen display 120 presents one or more video games advantageously incorporating a player avatar 180 that becomes stronger and/or smarter in proportion to the physical and/or mental capabilities of the player as an incentive for patient recovery. In an avatar communications mode, the player avatar and its corresponding physical and mental capabilities, are communicated to an external video game system, as described with respect to FIGS. 3-5, below.

In an embodiment, an avatar summary screen 122 is presented in the game play mode 102 illustrating the player's selected avatar 180 and indicators 190 of the avatar's accumulated physical strength and mental prowess. With respect to physical strength, the physiological monitor 100 is in wireless or wired communications with, for example, exercise equipment so as to incentivize patients recovering from, say, accidents or surgery to track physical exercise and healing progress. With respect to mental prowess, the physiological monitor 100 is in communications with mental skill test results, where the mental skills are either presented by the physiological monitor 100 itself in a mental challenge mode or input to the monitor 100 from external indicators of mental achievements, such as student report cards and standardized test results, to name a few.

In other embodiments, the physiological monitor 100 measures, records and tracks a person's physiological measurements such as resting heart rate, cholesterol, blood pressure among other physiological parameters. The person's avatar becomes physically stronger according to a health index based upon these parameters. Likewise, if a person passes certain quizzes or has a report card with straight A's, that person's avatar gets stronger and smarter for games simulating physical competition, such as racing, sports and combat. Advantageously, the physiological monitor 100 helps patients recovering from a stroke, provides a sports training tool for athletes and functions as a student teaching device, as a few examples.

Figure 2B:
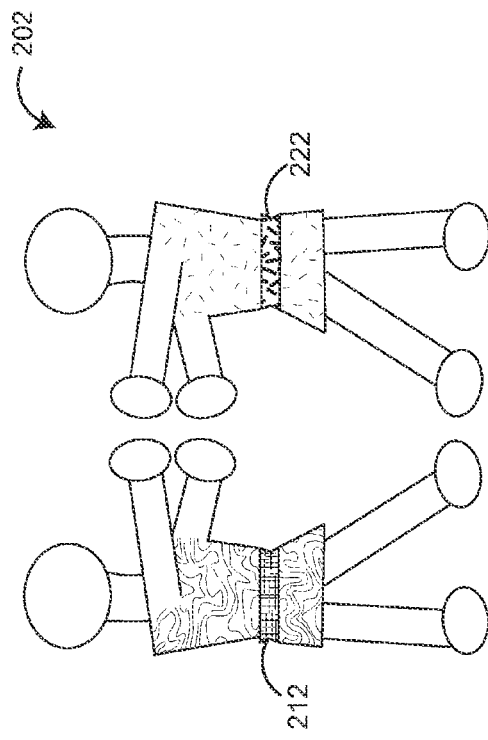
FIGS. 2A-C are avatar illustrations incorporating healthcare therapy incentives.
Figure 2C:
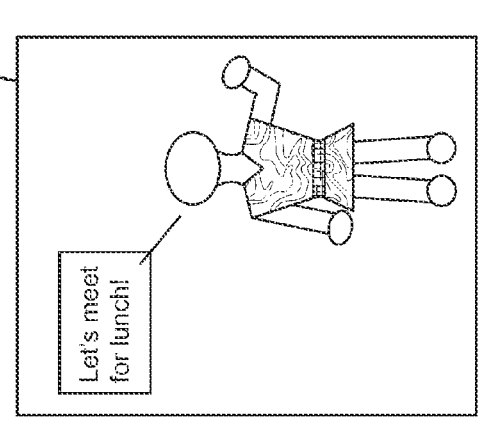
Figure 2A:
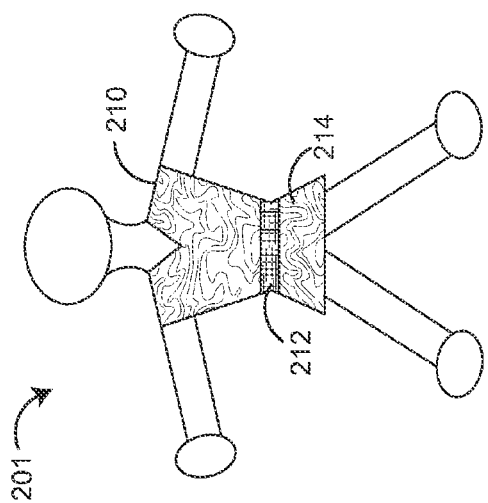

FIGS. 2A-C illustrate avatars incorporating healthcare therapy incentives. As shown in FIG. 2A, a physiological monitor 110 (FIG. 1A) allows a patient or other user to construct an avatar 201. The avatar's clothing or other external characteristics may overtly display the avatar's physical or mental strength 190 (FIG. 1B) as earned by the patient via improved physiological wellness or mental fitness tests measured by the monitor 110 (FIG. 1A) or provided externally, as described below. In an embodiment, the avatar has clothing 210 that reflects earned physical/mental accomplishments/improvements. In an exemplar embodiment, the avatar's belt color indicates earned physical strength and the avatar's tunic or dress color indicates earned mental strength. For example, a black belt and a bright colored tunic indicates an avatar with high physical and mental strength as the result of high physical and mental test scores and other real-world physical and mental accomplishments. As shown in FIG. 2B, earned avatar physical and mental strength are rewarded through video gaming, such as avatar combat, races and other player contests. As shown in FIG. 2C, avatar rewards may also be displayed on emails, Internet posts and other electronic communications.

Figure 3:
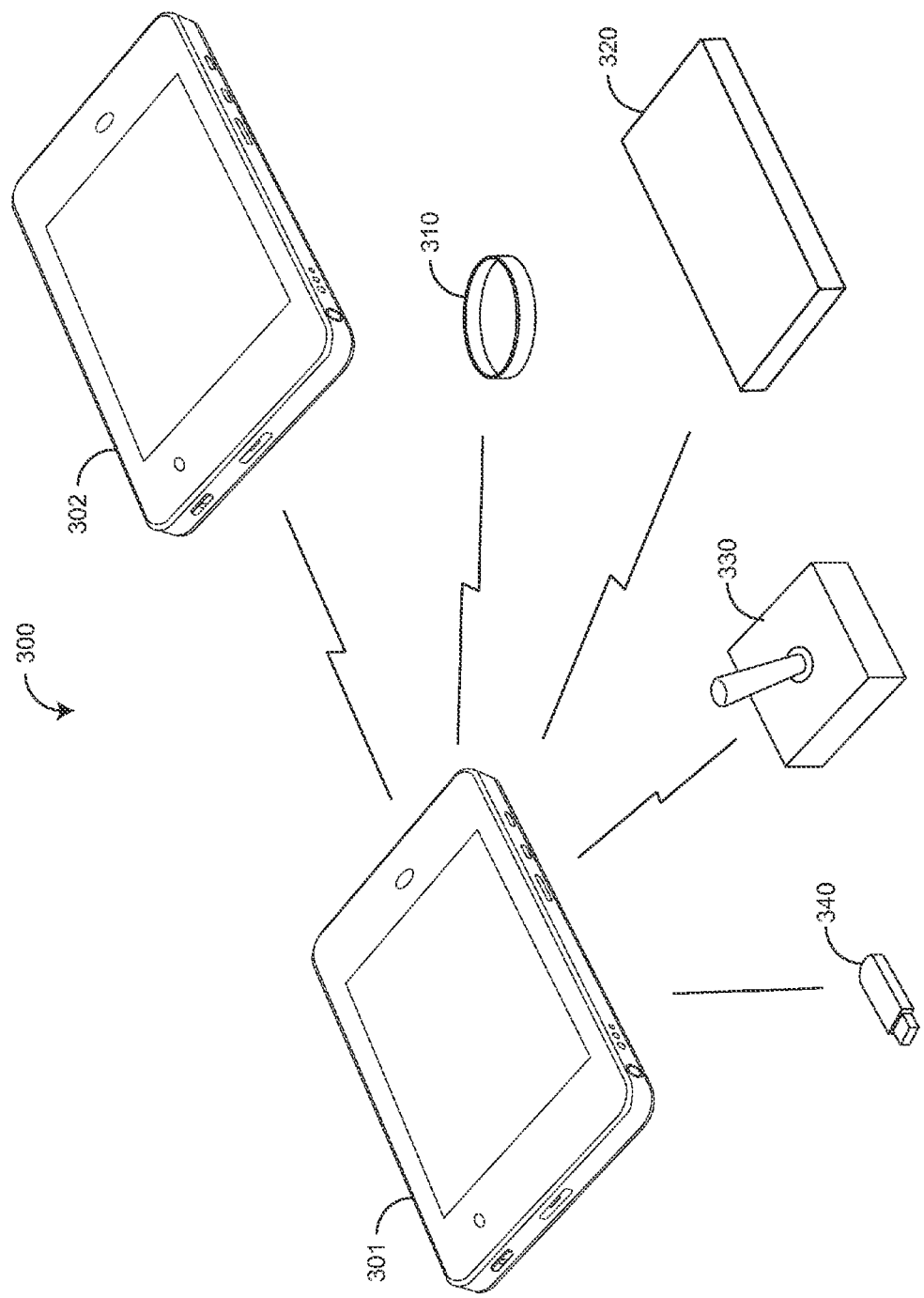
FIG. 3 are perspective views of physiological monitors and interfaced devices for incentivizing healthcare therapy.

FIG. 3 illustrate physiological monitors and interfaced devices for incentivizing healthcare therapy. The video game may be incorporated within one physiological monitor 301 for single player games or incorporated within linked physiological monitors 301, 302 for multiple-player games, as described with respect to FIG. 4, below. Alternatively, a monitor 301 may be interfaced with an external video game system 320 that resides locally or in the cloud, such as an online gaming center 540 (FIG. 5). Physiological data for constructing an avatar's physical strength may be derived by a physiological monitor 301, such as described with respect to FIG. 1, above, game play on an external video player 320, data from wearable activity devices such as fitness bracelets 310, data directly downloaded from a memory device such as a USB key 340 or from physiological data, game play, test scores, report cards 510-540 (FIG. 5) accessed via the cloud 10, as described with respect to FIG. 5, below. Similarly, mental prowess may be assessed by mental ability tests provided by physiological monitor 301, such as described with respect to FIG. 1, above, or from mental prowess data gathered via the cloud or other external sources, such as school grades and standardized test scores, as described with respect to FIG. 5, above. Video game play on a monitor 301 may also be enhanced by interfaced game play devices, such as a joystick 440.

Figure 4:
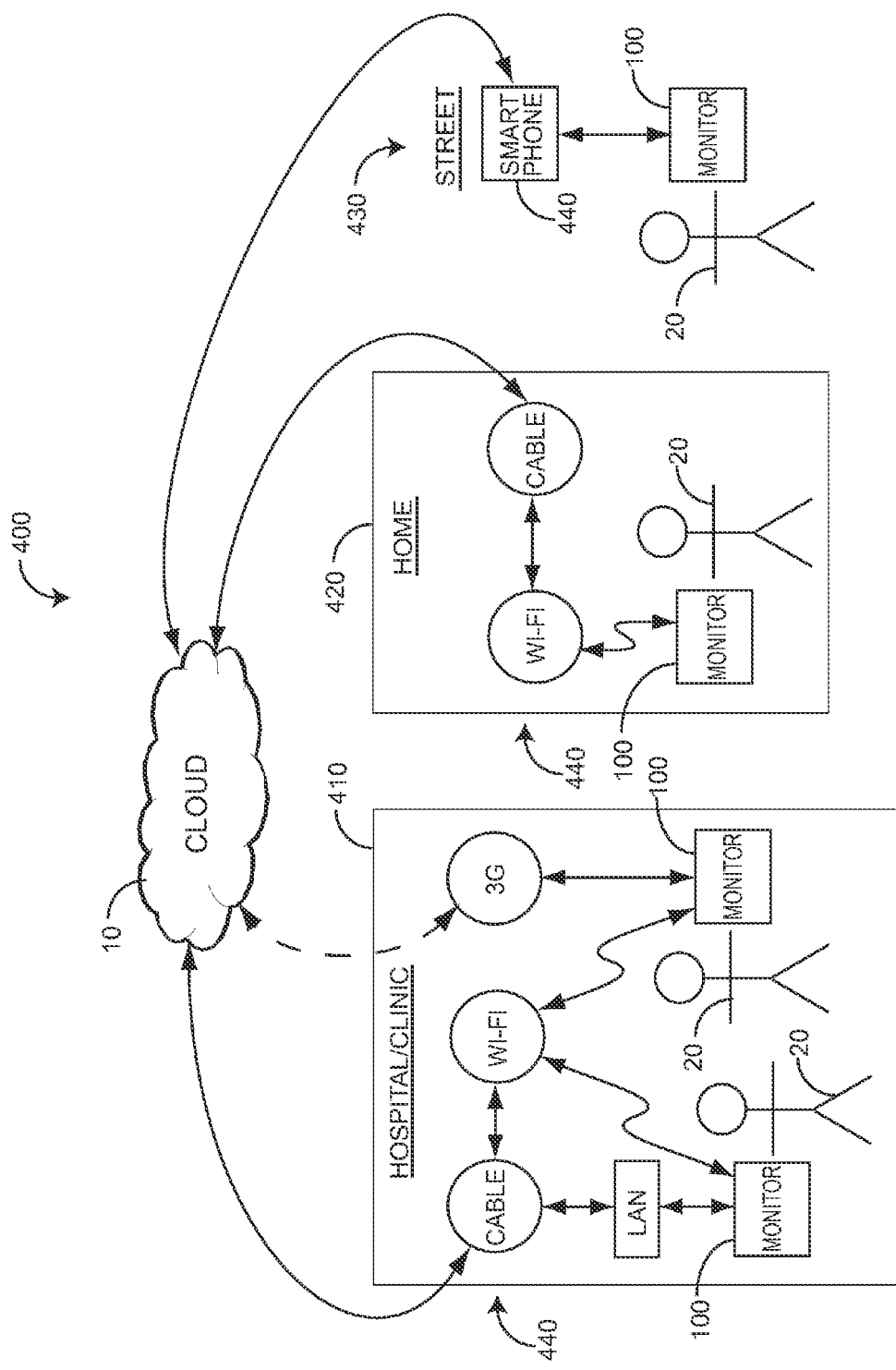
FIG. 4 is a block diagram of physiological monitor communications for incentivizing healthcare therapy.
Figure 5:
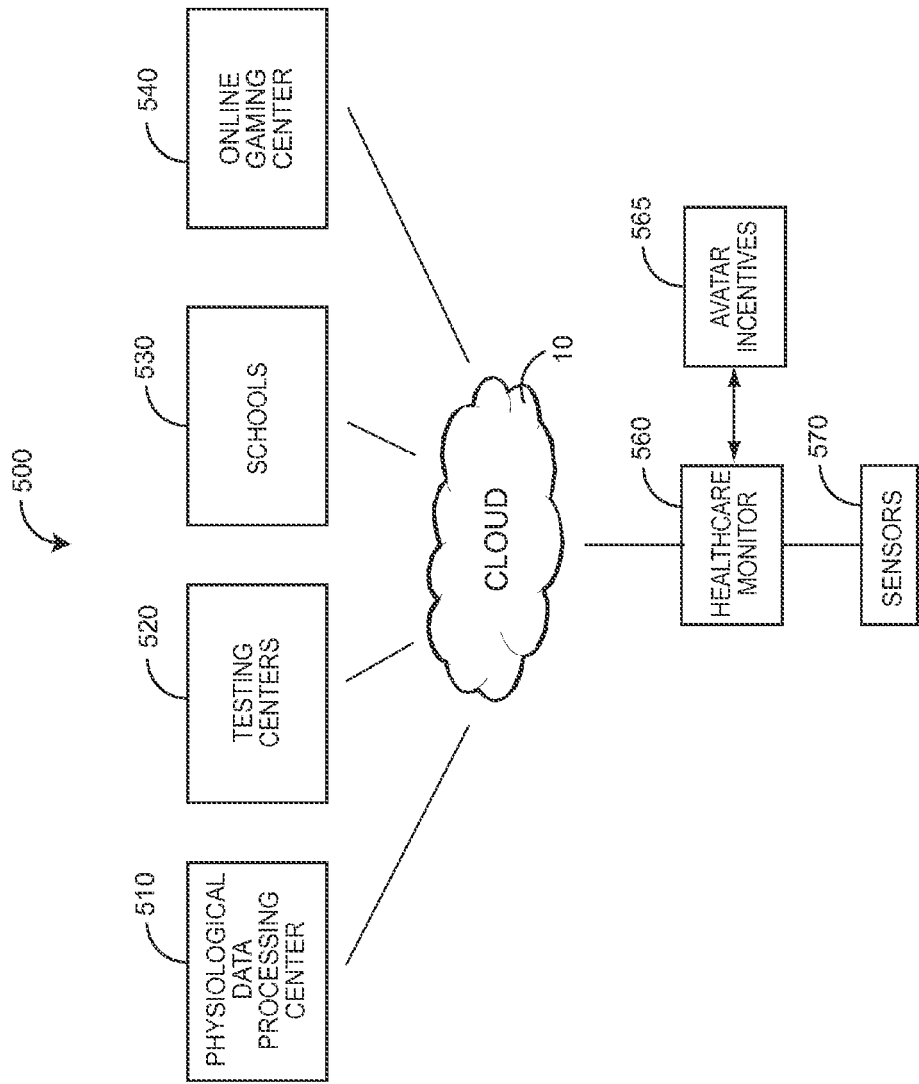
FIG. 5 is a block diagram of a cloud-based physiological monitoring system for avatar-incentive healthcare therapy.

FIG. 4 illustrates physiological monitor communications for incentivizing healthcare therapy. A cloud-based monitor communications system 400 has a cloud server 10 in communications with various physiological monitors 100. In this manner, monitor users 20 may freely network with each other whether located in various hospitals/clinics 410, at home 420, on the street 430 or any location remote from the cloud server 10. Data is transmitted from monitors 100 to the cloud server 10 via wired (e.g. LAN) or wireless (e.g. Wi-Fi) local networks to wide area media, such as Internet cable, telecommunications (e.g. 3G) networks or cellular networks 440. These wide area media, in turn, are in communications with the cloud server 10, which calculates physiological parameters or simply provides patient-to-patient communications including conversations or interactive gaming through their avatars, as described above.

FIG. 5 illustrates a cloud-based physiological monitoring system for avatar-incentive healthcare therapy. A healthcare monitor 560, such as described with respect to FIG. 1 (100), above, incorporating earned avatar incentives, also described above, may be in communications with a physiological data processing center 510, testing centers 520, schools 530 and online gaming centers 540. Physiological data for determining avatar physical strength may be determined from the physiological data processing center 510 and received by the monitor 560. Likewise, data for determining avatar mental acuity may be determined from standardized testing centers 520, e.g. from standard tests such as PSAT, SAT, GMAT, GRE etc. Avatar mental acuity may also be determined from various schools via authorized access to a particular student's grades 530. Further, earned avatar incentives can be exported to and used within games provided by online gaming centers 540. Avatar-incentive healthcare therapy has been disclosed in detail in connection with various embodiments. These embodiments are disclosed by way of examples only and are not to limit the scope of the claims that follow. One of ordinary skill in the art will appreciate many variations and modifications.

What is claimed is:

1. A method of generating a computer avatar of a person in a gaming software, the method comprising:
    receiving a physiological assessment responsive to a measurement from a physiological monitor;
    determining one or more characteristics of a computer avatar according to the physiological assessment;
    constructing the computer avatar that reflects the one or more characteristics;
    utilizing the computer avatar in a gaming software; and
    changing a performance capability of the computer avatar based on the determined one or more characteristics according to the physiological assessment.

2. The method according to claim 1, wherein the physiological monitor comprises a wearable fitness monitor.

3. The method according to claim 1, wherein the one or more characteristic comprises clothing.

4. The method according to claim 1, wherein the gaming software is an online gaming software.

5. The method according to claim 1, wherein the one or more characteristics comprises a combat skill of the computer avatar.

6. The method according to claim 1, wherein the one or more characteristics comprises a racing skill of the computer avatar.

7. The method of claim 1, wherein the physiological assessment is responsive to tracking an exercise activity of the person.

8. A system for generating a computer avatar of a person in a gaming software, the system comprising one or more hardware processors configured to:
    receiving a physiological assessment responsive to a measurement from a physiological monitor;
    determining one or more characteristics of a computer avatar according to the physiological assessment; and
    changing a performance capability of the computer avatar in a gaming software based on the determined one or more characteristics according to the physiological assessment.

9. The method according to claim 1, wherein the physiological monitor comprises a wearable fitness monitor.

10. The method according to claim 1, wherein the one or more characteristics comprises a combat skill of the computer avatar.

11. The method according to claim 1, wherein the one or more characteristics comprises a racing skill of the computer avatar.

12. A method of generating a computer avatar of a person in a gaming software, the method comprising:
    determining a physical characteristic of a user based on a sensor configured to sense the physical characteristic of the user;
    constructing a computer avatar that reflects the person's physical characteristic;
    displaying the computer avatar on a display; and
    changing a performance capability of the computer avatar in a video game responsive to the person's physical characteristic.

13. The method of claim 12, wherein the sensor comprises a glucose sensor and the physical characteristic comprises a blood glucose level.

14. The method of claim 12, wherein the sensor comprises an optical sensor and the physical characteristic comprises a pulse rate.

15. The method of claim 12, wherein the sensor comprises an optical sensor and the physical characteristic comprises a blood oxygen saturation.

16. The method according to claim 12, wherein the physical characteristic comprises a respiration rate.

17. The method according to claim 12, wherein the physical characteristic comprises exercise performance.

18. The method according to claim 12, wherein the sensor is included in a wearable fitness device and the physical characteristic corresponds to fitness data measured by the sensor in the wearable fitness device.

19. The method according to claim 12, wherein the computer avatar is displayed via a video game system.

* * * * *